United States Patent
Mårdh

(10) Patent No.: US 6,497,874 B1
(45) Date of Patent: Dec. 24, 2002

(54) RECOMBINANT PHAGES

(76) Inventor: Sven Mårdh, S-582 25, Linköping (SE)

( * ) Notice: Subject to any disclaimer, the term of this patent is extended or adjusted under 35 U.S.C. 154(b) by 0 days.

(21) Appl. No.: 09/603,153

(22) Filed: Jun. 23, 2000

Related U.S. Application Data

(62) Division of application No. 09/117,798, filed as application No. PCT/SE97/00172 on Feb. 5, 1997, now abandoned.

(51) Int. Cl.[7] .......................... A01N 63/00; C12N 7/00; C12N 15/00
(52) U.S. Cl. .................. 424/93.2; 424/93.6; 435/235.1; 435/320.1
(58) Field of Search ................. 435/235.1; 424/93.1, 424/93.2, 133.1, 134.1, 135.1, 141.1, 150.1, 93.6, 320.1

(56) References Cited

U.S. PATENT DOCUMENTS 5,688,501 A * 11/1997 Merril et al. ............... 424/93.6

FOREIGN PATENT DOCUMENTS

| WO | WO 92/01047 | * | 1/1992 |
| WO | WO 92/09690 | | 6/1992 |
| WO | WO 95/16027 | | 6/1995 |

OTHER PUBLICATIONS

Orum et al., Nucleic Acids Research, vol. 21(19), p. 4491–4498, Sep. 25, 1993.*

Orum et al., Efficient methods for constructing comprehensive murine Fab antibody libraries displayed on phage, 1993, Nucleic Aids Research, vol. 21, No. 19, pp. 4491–4498.*

Orum; et al.–Nucleic Acids Research, vol. 21(19), p. 4491–4498, d: Sep. 25, 1993.

* cited by examiner

Primary Examiner—Scott D. Priebe
Assistant Examiner—Shin-Lin Chen

(57) ABSTRACT

The present invention relates to bacteriophages for use in the treatment or prophylaxis of bacterial infections, especially mucosal bacterial infections such as *Heliobacter pylori* infections, in particular, it relates to modified filamentous bacteriophages, e.g. M13 phages, for such use, which bacteriophages present at the surface a recombinant protein comprising (i) a first component derived from a bacteriophage surface protein; and (ii) a second component comprising variable region sequences of an antibody to provide a bacterial antigen binding site, said second component rendering said bacteriophage capable of binding to and thereby inhibiting growth of bacterial cells involved in the etiology of said infection.

1 Claim, No Drawings

RECOMBINANT PHAGES

This application is a divisional of application Ser. No. 09/117,798 filed Aug. 6, 1998, abandonded Apr. 4, 2000, which was the national stage of International Application number PCT/SE97/00172 filed Feb. 5, 1997.

TECHNICAL FIELD

This invention relates to bacteriophages useful for the treatment of bacterial infections, especially mucosal bacterial infections such as *Helicobacter pylori* infections.

BACKGROUND ART

Bacteriophages and Antibiotic Resistance

Resistance to antibiotics is a global problem of increasing medical and economical importance. There is thus a great need for alternative methods to eradicate bacteria which will circumvent the problem of such resistance.

A bacteriophage, or phage, is a virus which specifically infects bacteria. Phages bind to their host bacterium and transfer genes encoding various phage proteins. They utilize the protein-synthesizing machinery, amino acids etc., and the energy provided by the host bacterium for their replication (Maloy et al. (eds.): Microbial genetics. Jones and Bartlett Publishers, 1994).

Most phages lyse or by other mechanisms destroy specific strains of bacteria. The present invention stems from the realisation that genetic modification of phages, in particular filamentous bacteriophages, offers a means for designing new bacterium-specific phages capable of eradicating certain bacteria, e.g. *Helicobacter pylori*, and having the potential to overcome problems related to antibiotic resistance.

Filamentous Phages

*E. coli* cells bearing hair-like F-pili are hosts for filamentous phages such as M13, fd and f1. These Ff (F pili, filamentous) phages are nearly identical in sequence and behaviour (Rashed & Oberer (1986) Microbiological reviews 50, 401–427; Kornberg & Baker, in: DNA Replication, p. 557–570, W.H. Freeman and Co., New York 1992). Ff phages alone among the bacterial viruses do not produce a lytic infection, but rather induce a state in which the infected host cells produce and secrete phage particles without undergoing lysis.

The single-stranded genome of phage M13 encodes 10 different proteins. The DNA is enclosed in a protein coat comprised of approximately 2700 copies of the gene 8 protein (g8p). A viable M13 phage also expresses five copies of the 43 kDa gene 3 protein (g3p) on its tip, which protein is responsible for adsorption to *E. coli* pili. The gene 3 protein is anchored to the virus coat via the C-terminal part of the polypeptide chain, whereas the N-terminal globular domain is exposed and mediates the attachment of the phage to the tip of a host F pilus. By electron microscopy, the adsorption complex appears as a "knob-on-stem" structure at one end of the phage. During infection, the leader sequences of g3p and g8p direct the transport of these proteins into the inner membrane of the bacterial cell.

The Ff phages have gained popularity as cloning vectors because they have no physical constraints limiting the length of DNA that can be packaged and because they allow the easy purification of single-stranded DNA. A phagemid is a vector which carries both the M13 (single-stranded) and plasmid (double-stranded) origins of replication. Phagemids can be grown as plasmids or packaged as recombinant M13 phage with the aid of a helper phage such as M13K07 (Veira & Messing (1987) Methods in Enzymol. 153, 3–11).

Recombinant Antibody Production

Antibody molecules contain discrete fragments which can be isolated by protease digestion or produced by recombinant techniques. One such fragment is the Fv (fragment variable) which is composed only of the $V_L$ and $V_H$ regions of the antibody. In U.S. Pat. No. 4,946,778 a recombinant version of the Fv fragment, designated single-chain Fv (ScFv), is described, where the two variable regions are artificially joined with a neutral linker and expressed as a single polypeptide chain.

A technology for recombinant antibody production has been developed by McCafferty and coworkers (McCafferty (1990) Nature 348, 552–554; Winter & Milstein (1991) Nature 349, 293). This approach relies on a phage-display system in which $V_H$ (variable heavy) and $V_L$ (variable light) genes are cloned into a phage vector whereafter fragments of antibodies are expressed as fusion proteins displayed on the phage surface. With this approach, antibodies of defined specificity and affinity can be selected from a population. It has been suggested that antibodies isolated and manufactured in prokaryotic systems should be called "coliclonal" antibodies (Chiswell & McCafferty (1992) Trends in Biotechnology 10, 80–84).

The commercially available phagemid pCANTAB5 is designed such that antibody variable region genes can be cloned between the leader sequence and the main body of the M13 gene 3. The g3p leader sequence directs transport of the resulting fusion protein to the inner membrane and/or periplasm of *E. coli* where the main g3p domain attaches the fusion protein to the tip of the assembling phage. The expression of the antibody-g3p gene is controlled by an inducible lac promoter on the phagemid.

Helicobacter pyloriInfection

It is widely accepted that the bacterium *Helicobacter pylori* is the main cause of gastric and duodenal ulcer, responsible for 84% and 95%, respectively, of reported cases (Kuipers, E. L. et al. (1995) Aliment. Pharmacol. Ther. 9 (suppl.2), 59–69). *H. pylori* colonises the wall of the stomach, protected from the acid environment by a layer of mucus which lines the stomach wall, and by a metabolic process which enables the organism to secrete ammonia to neutralise acid.

Conventional antibiotic treatment appears to have little effect on *H. pylori*. This is probably due to: (i) poor access of the antimicrobial agent to the organism which is not directly exposed to the blood circulation; and (ii) rapid passage of many oral antibiotics through the stomach, or degradation of such antibiotics in the acid conditions of the stomach.

PURPOSE OF THE INVENTION

The purpose of the present invention is to provide new forms of treatment for eradication of bacteria, especially eradication of bacteria responsible for mucosal bacterial infections such as *Helicobacter pylori*. In particular, it provides filamentous bacteriophages genetically modified to have binding specificity towards another bacterial host for use in therapy.

Methods of treatment of mucosal bacterial infections based on recombinant phages are believed to be superior to conventional antibiotic treatment for several reasons, e.g. the following:

it will be possible to eradicate bacteria resistant to conventional antibiotics;

the high specificity of the recombinant phage towards specific bacterial species;

propagation of the phage is self-limiting;

in the case of *Helicobacter pylori* infections, the motility of *Helicobacter pylori* could help to distribute the phage to all parts of the gastric mucosa.

DISCLOSURE OF THE INVENTION

In the present description and examples, the terms "standard protocols" and "standard procedures" are to be understood as protocols and procedures found in an ordinary laboratory manual such as: Sambrook, J., Fritsch, E. F. and Maniatis, T. (1989) Molecular Cloning: A laboratory manual, 2nd Ed., Cold Spring Harbor Laboratory, Cold Spring Harbor, N.Y.

In a first aspect, this invention provides a modified bacteriophage for use in the treatment or prophylaxis of a bacterial infection, which bacteriophage presents at its surface a recombinant protein comprising (i) a first component derived from a bacteriophage surface protein; and (ii) a second component comprising variable region sequences of an antibody to provide a bacterial antigen binding site, said second component rendering said bacteriophage capable of binding to and thereby inhibiting growth of bacterial cells involved in the etiology of said infection.

The said modified bacteriophage can e.g. be a modified filamentous phage, such as a modified M13 phage.

The said bacterial infection can e.g. be a mucosal bacterial infection such as *Helicobacter pylori* infection. However, the present invention is not restricted to phages capable of incapacitating *Helicobacter pylori* cells, but rather comprises phages with altered properties which can be used for incapacitating a wide range of bacteria. It will be understood that a phage according to the invention which is specific for any bacterial species can be prepared by the skilled person on the basis of the present disclosure. Phages according to the invention are suitable for treatment of any mucosal bacterial infection accessible to the outside world. Examples of such mucosal epitheliums are nasal, lung, gastrointestinal tract, urinary bladder and vagina.

Examples of other bacterial infections which could be treated with phages according to the invention are:

infections in the urinary tract by *E. coli, Staphylococcus saprophyticus*, Klebsiella spp, Proteus spp or *Pseudomonas aeruginosa;* vaginal infections by Clamydia;

nose/toncillar/lung infections by Streptoccus, Staphylococcus, *Haemophilus influence,* Pneumococcus or *Mycoplasma pneumonic;* infections in the gastrointestinal tract by Salmonella, Shigella, Yersinia, *Campylobacter jejuni, Campylobacter coli,* Helicobacter, *Vibrio cholera* or *E. coli.*

The said first component of the recombinant protein mentioned above can preferably be derived from the protein responsible for adsorption of the unmodified form of said bacteriophage to bacterial pili, e.g. the g3p protein from a M13 phage.

The said second component of said recombinant-protein can e.g. comprise a recombinant single-chain Fv (ScFv) polypeptide. Consequently, the said recombinant protein can e.g. be a g3p-ScFv fusion protein.

In a preferred form, the bacteriophage according to the invention is a bacteriophage for use in the treatment or prophylaxis of *Helicobacter pylori* infection wherein the antibody variable region sequences of said recombinant polypeptide are variable region sequences of a monoclonal antibody selected from the monoclonal antibodies of hybridoma cell lines 5F8 (ECACC No.95121524), 2H6 (ECACC No.95121526) and 5D8 (ECACC No.95121527).

Thus, the bacteriophage according to the invention can e.g. be the modified M13 bacteriophage designated B8 deposited at the NCIMB under accession number NCIMB 40779, or a derivative thereof which retains the ability to bind and infect *Helicobacter pylori.*

Phages with the desired properties can be obtained by e.g. one of the following methods:

(a) Screening naturally occurring phages, or phage libraries containing phages expressing a multitude of variable antibody fragments. Phage libraries may be obtained e.g. from immune cells, from a large number of individuals. Due to the vast genetic variability, such large phage libraries are likely to comprise the desired, specific phage directed towards bacteria, to which the individuals previously have been exposed.

(b) Development of mutations in existing phages. Mutations occur in all living organisms including phages. The frequency of mutations may be increased, e.g. by chemical means or by means of short wavelength electromagnetic irradiation.

(c) Directed genetic modification of one or more amino acids, or other modifications of e.g. carbohydrate or lipid components, of the binding region of the phage, in order to increase the desired properties of the natural or recombinant phage. An example of this approach is further described in the experimental section. A bacteriophage according to the invention can thus be produced by a method comprising (a) isolating an antibody against a bacterial cell; (b) isolating the DNA encoding for a variable region of the heavy and light chains of the said antibody; and (c) introducing the said DNA into phage DNA so that the said antibody regions will be expressed on the surface of the phage.

In another aspect, the invention provides a pharmaceutical composition comprising a bacteriophage according to the invention in admixture with a pharmaceutically acceptable carrier or excipient.

Examples of suitable means of administration of phages according to the invention include:

spray for nasal and lung applications;

pre-treatment with omeprazole followed by phages suspended in bicarbonate buffers for the treatment of gastrointestinal mucosae;

mixtures of muco-adhesive gels (i.e. cellulose-based gels, polycarbophil, poloxamer etc.) for the gastric mucosa and vaginal mucosa;

bicarbonate buffers for use in the urinary bladder.

The number of phages to be administered can be determined by the skilled person. Depending on the type of infection, the number of phages to be administered can range from $10^4$ to $10^{10}$.

In yet another aspect, the invention provides a method for treatment of a bacterial infection in a mammal which comprises administering a bacteriophage or pharmaceutical composition according to the invention. The said bacterial infections can e.g. be mucosal bacterial infections such as *Helicobacter pylori* infections. Included in the invention is also the use of a bacteriophage according to the invention in the manufacture of a medicament for the treatment or prophylaxis of a mucosal bacterial infection, e.g. *Helicobacter pylori* infections. Further aspects of the invention are a hybridoma selected from 5F8 (ECACC No.95121524), 2H6 (ECACC No.95121526) and 5D8 (ECACC No.95121527), as well as a monoclonal antibody selected from the monoclonal antibodies produced by the said hybridomas. Hybridoma technology, in which antibody-producing B-cells from immunized animals are fused with myeloma cells, and resulting hybridoma cell lines producing the desired antibody are selected, is well known in the art.

EXAMPLES

Example 1

Production of Monoclonal Antibodies Against *H. pylori*

1.1. Antigen Preparation

*H. pylori* strains 17874, 25, 66, 253, and 1139 (obtained from Astra Hässle, Sweden) were cultured on columbia agar supplemented with 8.5% horse blood, 10% horse serum, 1% isovitalex under microaerophilic condition with Anaerocult C at +37° C.

Procedures described by Ma J-Y et al. (1994) Scand. J. Gastroenterol. 29, 961–965, were followed to prepare surface protein of *H. pylori*. Briefly, a total of 4 g of the five strains of *H. pylori* were incubated for 15 min at room temperature in 100 ml of 0.2 M glycine-HCl (pH 2.2). The pH was neutralized with 1 M NaOH. The antigen preparation was centrifuged at 10,000×g for 10 min at +4° C. The pellet was discarded and the supernatant was dialysed overnight against distilled water at +4° C. and further used as "*H. pylori* antigen preparation" or "*H. pylori* surface proteins".

1.2. Production of Monoclonal Antibody

Immunization procedure was carried out essentially as described by Cabero, J. L. et al. (1992) Acta Physiol. Scand. 144,369–378. In brief, 2 mg/ml of surface protein of *H. pylori* was emulsified with an equal volume of Freund's complete adjuvant at +4° C. Two female DBA/1 mice were injected into the hind footpads with single dose of 50 µl of antigen emulsion. 11 days after immunization, lymphocytes from popliteal lymph nodes were fused with mouse myeloma cells (sp2 line) by using 50% (w/w) PEG 4000. The cell fusion suspension was then distributed in five microtiter plates. All cells were grown in DMEM culture medium containing 10% fetal calf serum plus 50 µg/ml gentamycin.

1.3. Enzyme-linked Immunosorbent Assay (ELISA)

Immunoplates were coated with 50 µl of 0.05 M $Na_2CO_3$/NaHCO. buffer, pH 9.8 containing indicated antigen (10 µg/ml) and incubated overnight at +4° C. Free binding sites were blocked with PBS containing 0.05% Tween-20 (PBS-T) at +37° C. for 1 hour. Primary antibody supernatant was added and incubated at +37° C. for 1 hour. Goat anti-mouse IgG peroxidase conjugate was used as a secondary antibody. Bound peroxidase was detected with 0.04% (w/v) OPD and 14 mM hydrogen peroxide in 0.1 M citric acid/0.2 M $NaHPO_4$, pH 5. The plates were read at 492 run after stopping reaction by adding 2 M $H_2SO_4$. Washing with PBS-T was performed three times between each incubation.

1.4. Initial Screening

From the fusion of lymph node cells and myeloma cells, 45 hybridoma clones were positive against *H. pylori* surface proteins by ELISA. 8 of them distinctly stained *H. pylori* taken from agar plate culture by means of immunohistochemistry. Hybridoma clones designated 2H6 (ECACC No. 95121526), 5D8 (ECACC No. 95121527), and 5F8 (ECACC No. 95121524) gave a stronger reaction against *H. pylori* than others and were chosen for further studies.

Example 2

Production of Recombinant M13 Phage Against *H. pylori*

2.1. Materials

QuickPrep mRNA purification kit™, Mouse ScFv Module kit™ Expression Module kit™, Detection Module Kit™, SfiI, NotI, T4 DNA ligase and Anti-M13 sheep antibody were obtained from Pharmacia Biotech (Uppsala, Sweden). dNTPs mix, 10×PCR buffer and AmpliTaq DNA polymerase were purchased from Perkin Elmer. Bacto-yeast extract, Bacto-tryptone, Bacto agar was purchased from Difco Laboratories (Detroit, Mich. USA). Columbia agar plates and brucella broth were obtained from Department of Microbiology (Linköping University, Sweden). Anaerocult®C was obtained from Merck (Germany). SlowFade™ antifade kit was obtained from Molecular Probes Inc. (U.S.A.).

2.2. Construction of Phage Antibody Library

The Recombinant Phage Antibody System™ (Pharmacia) was used to express fragments of antibodies as fusion proteins displayed on the phage surface.

Total mRNA was isolated from hybridoma cell lines (2H6, 5D8, and 5F8) and purified by affinity chromatography on oligo(dT)-cellulose, using QuickPrep mRNA Purification Kit™ (Pharmacia).

The following steps were performed using the Mouse ScFv Module Kit™:

First-strand cDNA was synthesized from hybridoma mRNA by using reverse transcriptase and primer mixes provided with the Mouse ScFv Module Kit™.

cDNA corresponding to the variable regions of the heavy and light chains of mAbs was amplified with different primers ($V_H$ and $V_L$ chain primers, provided with the kit) by means of polymerase chain reaction (PCR). The $V_H$ and $V_L$ chains were analyzed by electrophoresis on a 1.5% agarose gel. Single bands at the correct size for $V_H$ (340 bp) and $V_L$ (325 bp) chain were obtained.

The amplified $V_H$ and $V_L$ chains were purified and isolated by electrophoresis on a 1% agarose gel and were then assembled into a single-chain Fv (ScFv) gene using a DNA linker fragment provided with the kit. The linker fragment was constructed such that one end annealed to the 3'-end of the heavy chain while the other end hybridized with the 5'-end of the light chain. A single band at correct size for a ScFv gene (750 bp) was observed after electrophoresis.

The assembled antibody ScFv DNA fragment was amplified with a set of oligonucleotide primers (provided with the kit) that introduced NotI and SfiI restriction sites. The fragment was purified on a spun column (provided with the kit) to remove linkers, dNTPs and Taq DNA polymerase. The ScFv fragment was digested with NotI and SfiI to generate cohesive ends for ligation to the pCANTAB5 vector.

The following steps were performed using the Expression Module Kit™:

The ScFv fragment was ligated to the phagemid vector pCANTAB5 (provided with the kit), previously digested with NotI and SfiI to generate cohesive ends. T4 DNA ligase was used to join the ends of the fragment with corresponding ends of the phagemid. The ScFv fragment was then oriented in the proper direction, adjacent to and in frame with the M13 gene 3, for expression of the ScFv-g3p fusion protein.

*E. coli* TG1 cells (provided with the kit) were made competent and transformed with the recombinant phagemid, containing a lac promoter and an ampicillin resistance marker. The transformed cells were grown at +30° C. in a medium containing glucose and ampicillin. $3.2 \times 10^4$ ScFv clones were obtained. Ampicillin resistant colonies were scraped into medium to generate a library stock.

Ampicillin resistant cells were infected with the helper phage M13K07 (provided with the kit), containing a kanamycin resistance marker, and grown in a glucose-deficient medium containing ampicillin and kanamycin. In the absence of glucose, the lac promotor present on the phagemid was no longer repressed. Phage particles displaying recombinant antibody fragments on their tips were produced and released from the cells.

Phage-displayed antibodies capable of binding *H. pylori* antigen were selected by panning against the antigen. A culture flask was coated with 5 ml of *H. pylori* surface protein (15 μg/ml in 50 mM sodium carbonate buffer, pH 9.6) overnight. After three washes with PBS, the flask containing 10 ml of 1% BSA (w/v) in PBS was incubated at +37° C. for 1 h. Following three washes with PBS, the flask was incubated at +37° C. for 2 h in phage supernatant (medium containing phage). The flask was then washed 20 times with PBS containing 0.1% (w/v) Tween-20 and 20 times with PBS. Bound phage particles were then eluted by adding 1 ml of 100 mM triethylamine with gentle shaking for 10 min and immediately neutralized with 0.5 ml of 1 M Tris-HCl, pH 7.4.

The eluted phage was used to infect log-phase *E. coli* TG1 cells on the SOBAG agar containing 2% Bacto-tryptone, 0.5% Bacto-yeast extract, 0.05% NaCl, 0.01 M $MgCl_2$, 0.01% glucose and 0.01% ampicillin. Colonies were picked, transferred, grown and rescued again with M13K07.

After the first round of selection by counting 100 clones, 6% of clones from the microtiter plate rescue were positive against antigen preparation of *H. pylori* in an ELISA. In a third round of selection from the microtiter plate rescue, 95% of phage antibodies from individual clones reacted with the *H. pylori* antigens.

In a phage ELISA using the *H. pylori* antigen preparation as antigen, the recombinant phage B8 has a titre 10-fold higher than the helper phage (wide phage). Phage B8 (NCIMB No. 40779) was chosen for further analysis.

Example 3

ELISA

The phage-displayed recombinant antibodies were detected and identified in an enzyme-linked immunosorbent assay (ELISA), using the Detection Module Kit™.

A 96-well micro titre plate was coated with 200 μl of *H. pylori* antigen (10 μg/ml in 50 mM $Na_2CO_3$/$NaHCO_3$, pH 9.6) and incubated overnight at +4° C. The wells were washed with PBS containing 0.05% Tween 20 (PBS-T) for three times and then blocked with 300 μl of PBS containing 1% BSA for 1 hour at +37° C. Recombinant phage antibodies were diluted with an equal volume of 1% BSA/PBS and incubated for 20 min at room temperature. After washing, $5 \times 10^{10}$ phage transducing units were added (200 μl/well) and incubated for 2 hours at +37° C.

The wells were washed with PBS-T three times and then HRP/Anti M13 conjugate supplied in the Detection Module kit, diluted 1:5000 in 1% BSA/PBS was added and incubated for 1 hour at +37° C. The wells were washed for three times with PBS-T and then 2'2'-Azino-Bis(3-Ethylbenzthiazoline-6-Sulfonic Acid) Diammonium (ABTS) and $H_2O_2$ was added as peroxidase substrate and incubated at room temperature for 30 min. The absorbance was read at 405 nm using a computerized ELISA reader. Ovalbumin (10 μg/ml in PBS) was used as control antigen. Helper phage was used as a negative control. The results verified that the recombinant phage B8 specifically bound to the *H. pylori* surface antigen.

Example 4

Immunoblotting

Proteins of *H. pylori* antigen preparation were separated by means of polyacrylamide gel electrophoresis in SDS-PAGE (10 μg proteins/well) and were then transferred to the nitrocellulose paper in a mini trans-blot electrophoretic transfer cell (BioRad, Richmond, Calif., USA). The nitrocellulose paper was blocked with 10% BSA in PBS containing 0.1% Tween 20 for 1 h at room temperature with gentle shaking. Phage B8 ($10^{11}$ transducing units/ml) was then added and incubated together with the nitrocellulose paper overnight during gentle shaking at +4° C. Omission of primary antibody was used as a negative control. After washing with PBS-0.1% Tween 20, the nitrocellulose paper was incubated with HRP/anti-M13 conjugate (1:5000 dilution in blocking buffer) for 1 hour with shaking. Detection of binding was carried out by using ECL Detection Kit (Amersham, UK).

After staining the nitrocellulose paper with amido black, the major bands corresponded to proteins of 64 kDa, 36 kDa, 31 kDa and 27 kDa. Pooled MAbs (2H6, 5D8, and 5F8 corresponding to the hybridomas used for phage construction) reacted with the bands of 32 kDa and 64 kDa. A similar staining was obtained by immunoblotting with phage antibody B8. This result indicated that the genes of the variable heavy and light chains corresponding to the *H. pylori* specific monoclonal antibodies were correctly expressed on the phage.

Example 5

Effects of Recombinant Phage on Bacteria

In the following experiments, bacteria were cultured at +37° C. in Brucella broth containing 5% fetal calf serum in an atmosphere containing 10% $CO_2$ and 5% $O_2$.

The experiment was started ("Time 0") when 20 μl from the bacterial stock was mixed with 10 ml broth. CFU (colony forming units) per ml culture was determined at the indicated time points by diluting aliquots of the cultures in PBS and spreading the dilutions on agar plates. The plates were incubated for two days at +37° C. and the number of colonies of each plate was counted.

5.1. Time-dependent Effect

The time-dependent effect of the recombinant phage B8 on growth of *H. pylori* strain 17874 was investigated by measuring CFU for three days with or without phage (Table 1). $10^6$ phages were added ("+Phage") to 10 ml medium at Time 0. In the control ("−Phage") no phages were added.

After 3 days, CFU had increased about 5 orders of magnitude in the absence of the recombinant phage. After one day in presence of the phage, there was a drop of CFU by about one order of magnitude and the broth culture changed appearance from a turbid to a less turbid solution.

5.2. Effect on Various Bacterial Strains

*H. pylori* laboratory strains 17874, 1139 and 244, together with *Staphylococcus aureus*, ATCC 29213, and *E. coli* TG1 were cultured with or without phage ($10^6$ phages to 10 ml medium) for 24 h. CFU was analyzed at Time 0 and at 24 h (Table 2). The recombinant phage decreased CFU of the three *H. pylori* strains tested but did not affect Staphylococcus or *E. coli*. *H. pylori* 17874 was not affected by the helper phage M13K07 used as a control

5.3. Effect on H. pylori Strains

In a second experiment (Table 3), *H. pylori* strains 17874, 1139, 253, 25 and 66 were tested together with Streptococcus (Raf M87). Without phage, CFU increased during the 24 h incubation in all the bacteria tested. However, in culture with the recombinant phage present ($10^6$ phages to 10 ml medium at Time 0), the CFU values of the *H. pylori* strains 17874, 1139 and 25 were reduced in number and the growth rate of strains 253 and 66 were strongly reduced compared to the controls. Thus all *H. pylori* strains tested were affected by the phages.

Example 6

Immunofluorescent Staining of *H. pylori*

Phage antibody B8 was concentrated by PEG precipitation and immunofluorescent staining was performed on the *H. pylori* (17874 strain) taken from culture.

The following stock reagents were prepared to perform immunofluorescent staining:

Reagent A: $10^{12}$ transducing units/ml of phage antibodies was diluted 1:1 with 1% BSA/PBS;
Reagent B: sheep anti-M13 IgG diluted with 1% BSA/PBS;
Reagent C: anti-sheep IgFITC conjugate dilute 1:100 in 1% BSA/PBS;
Reagent D: 1 mg (w/v) of pronase in PBS.

Three days after culture, *H. pylori* (5 different strains), *Staphylococcus aureus* (ATCC 29213), and Streptococcus (Raf M 87) were separately suspended in PBS containing 1% BSA. 20 μl of each bacteria suspension were added onto glass slides. The bacteria were air dried and fixed in neutral formalin for 2 min, then washed by dipping slides six times into water and air dried at room temperature. Brief treatment in reagent D increased signal-to-noise ratio when sample slides were compared with controls. The slides were consecutively incubated with 30 μl of reagents A, B and C, for 30 min each, and washed in PBS between incubations. The slides were air dried and 1 drop of SlowFade was added before covering. All incubations were performed at room temperature. Negative control was performed by omitting the primary antibody The results showed that *H. pylori* was positively stained with phage antibody The results indicate a good agreement with the CFU values obtained from culture experiments. Thus the expression of a specific antigen on the surface of the bacteria appears to be a prerequisite for execution of the biological effect by phage is B8.

Deposit of Biological Material

The following hybridoma clones have been deposited under the Budapest Treaty at the European Collection of Animal Cell Cultures (ECACC), Salisbury, Wiltshire, U.K., on Dec. 15, 1995:

2H6 (ECACC No. 95121526)

5D8 (ECACC No. 95121527)

5F8 (ECACC No. 95121524)

The recombinant phage B8 has been deposited under the Budapest Treaty at the National Collections of Industrial and Marine Bacteria (NCIMB), Aberdeen, Scotland, on Dec. 20, 1995 with accession number NCIMB 40779.

TABLE 1

|  | −Phage | +Phage B8 |
|---|---|---|
|  | CFU/ml |  |
| Time 0 | $5 \times 10^4$ | $4 \times 10^4$ |
| 24 h. | $1.9 \times 10^7$ | $8 \times 10^3$ |
| 48 h. | $1.75 \times 10^8$ | $9.5 \times 10^3$ |
| 72 h | $4 \times 10^8$ | $3 \times 10^6$ |

TABLE 2

|  |  | *H. pylori* | | | | |
|---|---|---|---|---|---|---|
|  |  | 17874 | 1139 | 244 | Staph. | *E. Coli* |
|  |  |  |  | CFU/ml |  |  |
| No phage | 0 h. | $2.1 \times 10^4$ | $4.7 \times 10^4$ | $10^4$ | $7.8 \times 10^7$ | $2.6 \times 10^6$ |
| phage | 24 h. | $5.8 \times 10^6$ | $1.5 \times 10^7$ | $3.1 \times 10^5$ | $10^{10}$ | $4.4 \times 10^8$ |
| Phage B8 | 0 h. | $2.8 \times 10^4$ | $4.3 \times 10^4$ | $10^4$ | $2.1 \times 10^8$ | $2.6 \times 10^6$ |
|  | 24 h. | $4 \times 10^2$ | $10^2$ | $10^3$ | $8 \times 10^9$ | $4.2 \times 10^8$ |
| Phage | 0 h | $3.9 \times 10^4$ |  | (not determined) | | |
| M13K07 | 24 h. | $4 \times 10^6$ |  | (not determined) | | |

TABLE 3

|  | −Phage | | +Phage B8 | |
|---|---|---|---|---|
|  | 0 h. | 24 h. | 0 h. | 24 h. |
| 17874 | $1.5 \times 10^4$ | $5 \times 10^6$ | $1.3 \times 10^4$ | $2 \times 10^2$ |
| 1139 | $10^4$ | $7 \times 10^6$ | $9 \times 10^3$ | $1.1 \times 10^3$ |
| 253 | $1.1 \times 10^4$ | $1.7 \times 10^7$ | $1.3 \times 10^4$ | $4 \times 10^5$ |
| 25 | $1.4 \times 10^4$ | $9 \times 10^7$ | $7 \times 10^3$ | $3 \times 10^2$ |
| 66 | $1.4 \times 10^4$ | $2.1 \times 10^7$ | $1.4 \times 10^4$ | $4 \times 10^4$ |
| Strept. | $2.3 \times 10^7$ | $5.6 \times 10^7$ | $1.9 \times 10^7$ | $5.8 \times 10^7$ |

What is claimed is:

1. An M13 bacteriophage B8 having the accession number NCIMB 40779.

* * * * *